United States Patent

Dubuffet et al.

(10) Patent No.: US 7,220,776 B2
(45) Date of Patent: May 22, 2007

(54) METHOD FOR THE SYNTHESIS OF PERINDOPRIL AND THE PHARMACEUTICALLY ACCEPTABLE SALTS THEREOF

(75) Inventors: Thierry Dubuffet, Autretot (FR); Jean-Pierre Lecouve, Le Havre (FR)

(73) Assignee: LES Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/562,950

(22) PCT Filed: Jun. 28, 2004

(86) PCT No.: PCT/FR2004/001638

§ 371 (c)(1),
(2), (4) Date: Dec. 23, 2005

(87) PCT Pub. No.: WO2005/005461

PCT Pub. Date: Jan. 20, 2005

(65) Prior Publication Data

US 2006/0148884 A1    Jul. 6, 2006

(30) Foreign Application Priority Data

Jun. 30, 2003  (EP) .................... 03291600

(51) Int. Cl.
*A61K 31/405* (2006.01)
*C07D 209/42* (2006.01)

(52) U.S. Cl. ...................... 514/419; 548/492
(58) Field of Classification Search ............... 514/419; 548/492
See application file for complete search history.

(56) References Cited

U.S. PATENT DOCUMENTS

2006/0178421 A1 *  8/2006  Dubuffet et al. ............ 514/419

FOREIGN PATENT DOCUMENTS

EP    1321471    6/2003

OTHER PUBLICATIONS

Suh J. T. et al., "Angiotensin-converting enzyme inhibitors: N-substituted glycine derivatives" European Journal of Medicinal Chemistry, vol. 20, No. 6, 1985, pp. 563-570.
International Search Report: PCT/FR2004/001638, Nov. 8, 2004.
International Preliminary Examination Report for PCT FR2004 001638, May 11, 2006.

* cited by examiner

*Primary Examiner*—Kamal A. Saeed
(74) *Attorney, Agent, or Firm*—Hueschen and Sage

(57) ABSTRACT

Process for the synthesis of perindopril of formula (I):

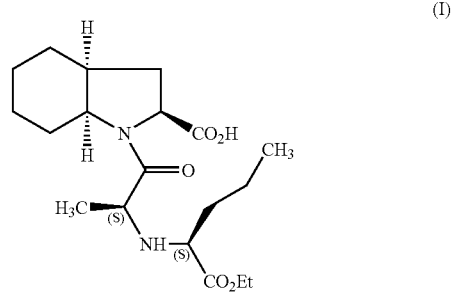

and its pharmaceutically acceptable salts.

5 Claims, No Drawings

METHOD FOR THE SYNTHESIS OF PERINDOPRIL AND THE PHARMACEUTICALLY ACCEPTABLE SALTS THEREOF

The present invention relates to a process for the synthesis of perindopril of formula (I):

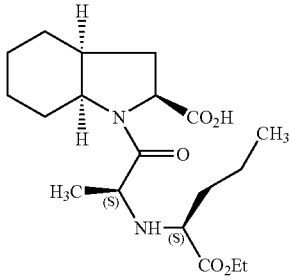

and its pharmaceutically acceptable salts.

Perindopril and its pharmaceutically acceptable salts, and more especially its tert-butylamine salt, have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in European patent specification EP 0 049 658.

In view of the pharmaceutical value of this compound, it has been important to be able to obtain it by an effective synthesis process, readily transposable to an industrial scale, that leads to perindopril in a good yield and with excellent purity starting from reasonably priced starting materials.

Patent specification EP 0 308 341 describes the synthesis of perindopril by the peptide-type coupling of (2S,3aS,7aS)-octahydroindole-2-carboxylic acid benzyl ester with N-[(S)-1-carboxybutyl]-(S)-alanine ethyl ester, followed by deprotection of the carboxylic group of the heterocycle by catalytic hydrogenation.

That process has the advantage of yielding perindopril in a good yield from starting materials for which industrial synthesis has already been described.

However, it also has drawbacks associated with the use of dicyclohexylcarbodiimide in the coupling step: the formation of coupling impurities, and of dicyclohexylurea, a by-product which is difficult to remove.

The Applicant has now developed a new process for the synthesis of perindopril that avoids the formation of those secondary products.

More specifically, the present invention relates to a process for the synthesis of perindopril and its pharmaceutically acceptable salts which is characterised in that the compound of formula (II):

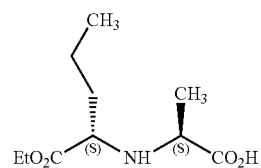

is reacted with a compound of formula (III):

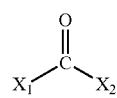

wherein $X_1$ and $X_2$, which may be identical or different, each represents a leaving group, to yield the compound of formula (IV):

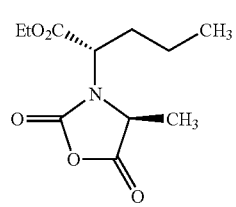

which is reacted with a compound of formula (V)

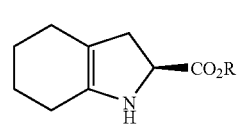

wherein R represents a hydrogen atom or a benzyl or linear or branched $(C_1-C_6)$alkyl group, or an addition salt thereof with a mineral or organic acid, to yield, after isolation, a compound of formula (VI):

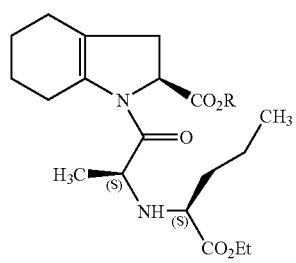

wherein R is as defined hereinbefore, which is hydrogenated in the presence of a catalyst such as, for example, palladium, platinum, rhodium or nickel, under a hydrogen pressure of from 1 to 30 bars, preferably from 1 to 10 bars, to yield, after deprotection where necessary of the acid function, perindopril of formula (I) which is converted, if desired, to a pharmaceutically acceptable salt such as the tert-butylamine salt.

Appropriate leaving groups $X_1$ and $X_2$ that may be mentioned, without implying any limitation, include the halogen atoms and the groups tosylate, mesylate, linear or branched $(C_1-C_6)$alkoxy, linear or branched $(C_1-C_6)$alkylthio, imidazolyl, benzimidazolyl, tetrazolyl, benzotetrazolyl, linear or branched trihalo-$(C_1-C_6)$alkyl, linear or branched trihalo-$(C_1-C_6)$alkoxy, and succinimidyloxy.

Preferred leaving groups $X_1$ and $X_2$ that may be mentioned include the chlorine atom and the imidazolyl and trichloromethoxy groups.

The Example below illustrates the invention but does not limit it in any way.

EXAMPLE (2S,3aS,7aS)-1-{(2S)-2-[(1S)-1-(Ethoxycarbonyl) butylamino]-propionyl}octahydro-1H-indole-2-carboxylic acid tert-butylamine salt Step A: Ethyl (2S)-2-[(4S)-4-methyl-2,5-dioxo-1,3-oxazolidin-3-yl]pentanoate Introduce into a reactor, at 0° C., 200 g of N-[(S)-ethoxycarbonyl-1-butyl]-(S)-alanine, 1.5 litres of toluene, and then 184 g of 1,1'-carbonyldiimidazole, then bring the temperature of the reaction mixture to 20° C. After stirring for 1 hour at 20° C., cool the mixture to 0° C. again, filter off the precipitate obtained, then evaporate the filtrate to yield the title product in a yield of 90%.

Step B: (2S)-{(2S)-2-[(1S)-1-(Ethoxycarbonyl)butylamino] propionyl}-2,3,4,5,6,7-hexahydro-1H-indole-2-carboxylic acid Introduce 200 g of (2S)-2,3,4,5,6,7-hexahydro-1H-indole-2-carboxylic acid and 1.5 litres of dichloromethane into a reactor, followed by 180 ml of triethylamine.

Subsequently, slowly add a solution of 290 g of the compound obtained in the above Step in 500 ml of dichloromethane and then stir for a further 1 hour at ambient temperature. After the addition of water, the reaction mixture is cooled to 15° C. and the pH is adjusted to 4.2 by the addition of a 2N hydrochloric acid solution. Following extraction, the organic phases are washed and then evaporated to yield the expected product.

Step C: (2S,3aS,7aS)-1-{(2S)-2-[1S)-1-(Ethoxycarbonyl) butylamino]propionyl}-octahydro-1H-indole-2-carboxylic acid Introduce into a hydrogenation vessel 200 g of the compound obtained in the above Step in solution in acetic acid, and then 5 g of 10% Pt/C. Hydrogenate under a pressure of 5 bars at ambient temperature until the theoretical amount of hydrogen has been absorbed.

Remove the catalyst by filtration, and then cool to from 0 to 5° C. and recover, by means of filtration, the solid obtained. Wash the cake and dry it to constant weight.

Step D: (2S,3aS,7aS)-1-{(2S)-2-[(1S)-1-(Ethoxycarbonyl) butylamino]propionyl}-octahydro-1H-indole-2-carboxylic acid tert-butylamine salt The compound obtained in the above Step (200 g) is dissolved in 2.8 litres of ethyl acetate, and then 40 g of tert-butylamine and 0.4 litre of ethyl acetate are added.

The suspension obtained is then refluxed until complete dissolution occurs, and the solution obtained is then filtered in the heated state, and cooled, with stirring, to a temperature of from 15 to 20° C.

The precipitate obtained is subsequently filtered off, made into a paste again with ethyl acetate, dried and then crushed to yield the expected product in a yield of 95%.

What is claimed is:

1. A process for the synthesis of perindopril of formula (I):

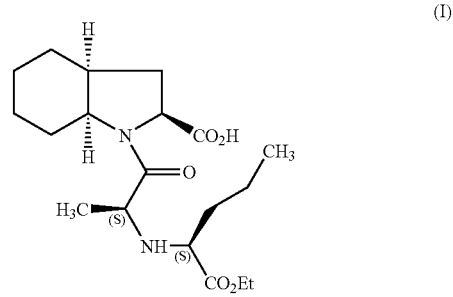

(I)

and pharmaceutically acceptable salts thereof, wherein a compound of formula (II):

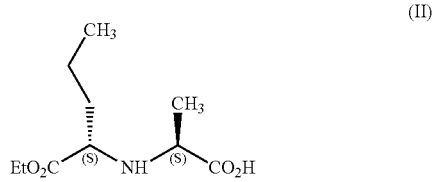

(II)

is reacted with a compound of formula (III):

(III)

wherein $X_1$ and $X_2$, which may be identical or different, each represent a leaving group, to yield a compound of formula (IV):

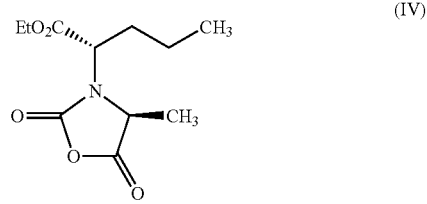

(IV)

which is reacted with a compound of formula (V):

(V)

wherein R represents hydrogen, benzyl or linear or branched $(C_1-C_6)$alkyl, or an addition salt thereof with a mineral or organic acid, to yield, after isolation, a compound of formula (VI):

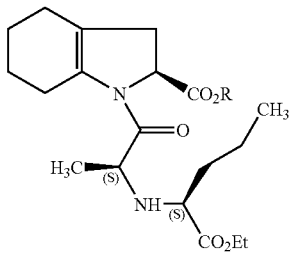

(VI)

which is hydrogenated in the presence of a catalyst, under a hydrogen pressure of from 1 to 30 bars, to yield, after deprotection of the acid function where necessary, perindopril of formula (I) which is converted, if desired, to a pharmaceutically acceptable salt.

2. The process of claim 1, wherein the hydrogen pressure in the hydrogenation reaction is from 1 to 10 bars.

3. The process of claim 1, wherein the catalyst is selected from palladium, platinum, rhodium and nickel.

4. The process of claim 1, wherein $X_1$ and $X_2$ each represent chlorine, imidazolyl or trichloromethoxy.

5. The process of claim 1 for the synthesis of perindopril in the form of its tert-butylamine salt.

* * * * *